United States Patent
Street

(10) Patent No.: US 10,842,603 B1
(45) Date of Patent: Nov. 24, 2020

(54) SUTURELESS VENTRAL HERNIA MESHING SYSTEM AND METHOD OF FIXATION

(71) Applicant: David Lee Street, Medford, OR (US)

(72) Inventor: David Lee Street, Medford, OR (US)

(*) Notice: Subject to any disclaimer, the term of this patent is extended or adjusted under 35 U.S.C. 154(b) by 194 days.

(21) Appl. No.: 16/048,586

(22) Filed: Jul. 30, 2018

Related U.S. Application Data

(60) Provisional application No. 62/572,607, filed on Oct. 16, 2017.

(51) Int. Cl.
   *A61F 2/00* (2006.01)

(52) U.S. Cl.
   CPC .... *A61F 2/0063* (2013.01); *A61F 2220/0016* (2013.01); *A61F 2230/0006* (2013.01); *A61F 2230/0069* (2013.01)

(58) Field of Classification Search
   CPC .......... A61F 2/0063; A61F 2/0077; A61F 2002/0068; A61F 2002/0072; A61F 2002/0086; A61F 2220/0016
   See application file for complete search history.

(56) References Cited

U.S. PATENT DOCUMENTS

| | | | | |
|---|---|---|---|---|
| 4,548,202 A * | 10/1985 | Duncan | ............ | A61B 17/0643 606/220 |
| 5,176,692 A * | 1/1993 | Wilk | ............ | A61B 17/0057 604/103 |
| 5,824,082 A * | 10/1998 | Brown | ............ | A61F 2/0063 623/11.11 |
| 6,171,318 B1 | 1/2001 | Kugel et al. | | |
| 6,224,616 B1 * | 5/2001 | Kugel | ............ | A61F 2/0063 128/898 |
| 6,290,708 B1 | 9/2001 | Kugel et al. | | |
| 6,425,900 B1 | 7/2002 | Knodel et al. | | |
| 6,712,822 B2 * | 3/2004 | Re | ............ | A61B 17/0642 606/75 |
| 6,893,452 B2 * | 5/2005 | Jacobs | ............ | A61B 17/064 606/215 |
| 7,156,862 B2 * | 1/2007 | Jacobs | ............ | A61B 17/064 606/215 |
| 7,172,615 B2 * | 2/2007 | Morriss | ............ | A61B 90/02 606/215 |
| 7,758,612 B2 * | 7/2010 | Shipp | ............ | A61B 17/064 600/142 |
| 8,114,101 B2 * | 2/2012 | Criscuolo | ............ | A61B 17/122 606/151 |
| 8,216,272 B2 | 7/2012 | Shipp | | |
| 8,343,176 B2 | 1/2013 | Crisuolo et al. | | |

(Continued)

*Primary Examiner* — Ryan J. Severson
(74) *Attorney, Agent, or Firm* — Jerry Haynes Law

(57) ABSTRACT

A sutureless ventral hernia meshing system and method of fixation is efficacious for fixating a surgical mesh panel to an abdominal wall for the purpose of hernia repair and prevention of hernia recurrence at the peripheral region of the mesh panel. The mesh panel comprises a hydrophilic face and a meshed face. A plurality of hollow anchors such as spikes or pins or hooks are disposed along the peripheral region of the mesh panel in a spaced apart relationship. A blunt quill or needle presses the hollow spikes or pins or hooks into the fascia around the hernia. The blunt quill or needle is removed after pressing the hollow pin into the fascia. In this manner, no sharp needle or suture is used. Tissue growth occurs in the cavity of the hollow spikes or pins or hooks to provide a sutureless anchor.

20 Claims, 6 Drawing Sheets

(56) References Cited

U.S. PATENT DOCUMENTS

| | | |
|---|---|---|
| 8,500,759 B2 | 8/2013 | Koyfman et al. |
| 8,500,762 B2 | 8/2013 | Sholev et al. |
| 8,641,699 B2 * | 2/2014 | Hansen ............... A61B 17/0057 606/1 |
| 8,852,215 B2 | 10/2014 | Criscuolo et al. |
| 8,920,370 B2 * | 12/2014 | Sholev .................. A61F 2/0063 604/103 |
| 8,940,017 B2 * | 1/2015 | Bell .................. A61M 39/0613 128/834 |
| 9,204,955 B2 * | 12/2015 | AlDahian .............. A61F 2/0063 |
| 9,295,538 B2 * | 3/2016 | Koyfman .............. A61F 2/0063 |
| 9,393,091 B2 * | 7/2016 | Khamis .............. A61B 17/0401 |
| 9,398,943 B2 * | 7/2016 | Criscuolo ............. A61F 2/0063 |
| 9,402,986 B2 * | 8/2016 | Bell .................. A61M 39/0613 |
| 9,486,218 B2 | 11/2016 | Criscuolo et al. |
| 9,492,261 B2 * | 11/2016 | Cohen .................... A61B 17/06 |
| 9,642,689 B2 | 5/2017 | Sholev et al. |
| 9,687,332 B2 * | 6/2017 | Sholev .................. A61F 2/0063 |
| 9,782,246 B2 * | 10/2017 | Khamis .............. A61B 17/0401 |
| 10,098,634 B2 * | 10/2018 | Shipp .................... A61B 17/068 |
| 10,117,734 B2 * | 11/2018 | Guo ................ A61B 17/06004 |
| 10,195,012 B2 * | 2/2019 | Peery .................... A61F 2/0063 |
| 10,258,449 B2 * | 4/2019 | Cohen .................... A61B 17/06 |
| 2002/0077661 A1 * | 6/2002 | Saadat .................. A61B 17/08 606/221 |
| 2002/0103494 A1 | 8/2002 | Pacey |
| 2003/0074021 A1 * | 4/2003 | Morriss .................. A61B 90/02 606/215 |
| 2004/0010275 A1 * | 1/2004 | Jacobs ................ A61B 17/064 606/153 |
| 2004/0260340 A1 * | 12/2004 | Jacobs ................... A61B 17/11 606/213 |
| 2005/0119694 A1 * | 6/2005 | Jacobs ................ A61B 17/064 606/213 |
| 2005/0192629 A1 * | 9/2005 | Saadat .................. A61F 5/0076 606/221 |
| 2005/0240222 A1 * | 10/2005 | Shipp .................... A61B 17/064 606/219 |
| 2009/0030434 A1 * | 1/2009 | Paz ...................... A61B 17/064 606/151 |
| 2009/0082792 A1 * | 3/2009 | Koyfman .............. A61F 2/0063 606/151 |
| 2011/0106113 A1 | 5/2011 | Tavakkolizadeh et al. |
| 2011/0160527 A1 * | 6/2011 | Khamis .............. A61B 17/0401 600/37 |
| 2013/0172915 A1 * | 7/2013 | Thomas ........... A61B 17/06166 606/151 |
| 2014/0094830 A1 * | 4/2014 | Sargeant ............... A61F 2/0063 606/151 |
| 2015/0272724 A1 * | 10/2015 | Griffin ...................... A61F 2/12 623/8 |
| 2016/0106878 A1 * | 4/2016 | Yang ...................... C08L 67/04 424/445 |
| 2016/0074034 A1 | 5/2016 | Shipp |
| 2016/0296314 A1 * | 10/2016 | Khamis .............. A61B 17/0401 |
| 2017/0231740 A1 * | 8/2017 | Peery .................... A61F 2/0063 606/151 |
| 2018/0028303 A1 * | 2/2018 | Guo ................ A61B 17/06004 |
| 2018/0221126 A1 * | 8/2018 | Igov .................... A61F 2/0063 |
| 2019/0021833 A1 * | 1/2019 | Guo ................ A61B 17/06004 |
| 2019/0117363 A1 * | 4/2019 | Felix .................... A61F 2/0063 |
| 2019/0142562 A1 * | 5/2019 | Peery .................... A61F 2/0063 |

* cited by examiner

SUTURELESS VENTRAL HERNIA MESHING SYSTEM AND METHOD OF FIXATION

CROSS-REFERENCE TO RELATED APPLICATIONS

This application claims priority from U.S. Provisional Application Ser. No. 62/572,607, entitled "Sutureless Ventral Hernia Meshing System and Method of Fixation", filed on Oct. 16, 2017, which application is hereby incorporated herein by reference in its entirety.

FIELD OF THE INVENTION

The present invention relates generally to a tissue aperture sutureless repair meshing system and method of fixation. More so, the present invention relates to a ventral hernia meshing system used to fixate a surgical mesh panel to an abdominal wall for the purpose of hernia repair and prevention of hernia recurrence at the peripheral region of the mesh panel.

BACKGROUND OF THE INVENTION

A hernia is a common medical condition in which an organ protrudes through an opening in its surrounding tissue, such as in the abdominal region. One common way of attaching the mesh to tissue is through the use of suture and needle. During hernia repair surgery it is often necessary to affix a section of mesh over the herniated tissue. This is often accomplished through the use of staples or sutures or other affixation type means.

Those skilled in the art will recognize that, the hernia is sometimes treated in a tension free repair, such as implementation of meshes and patches. The mesh may then be held in place by stapling or suturing it to underlying tissue. Sometimes tacks are placed at close intervals, preventing the bowels (or other organs) from passing between the mesh and the abdominal wall.

Specifically, internal forces exerted on the mesh are typically transferred to the muscle layer through these sutures. The sutures, in turn, concentrate these forces causing pain. Moreover, sutures have relatively low compliance compared to abdominal tissues, and therefore sutures may "pinch" when the muscle tissue contracts, similarly causing irritation to surrounding tissue. Furthermore, metal tacks (as described above) may occasionally dislodge from the abdominal wall, permitting them to irritate other tissue as they move within the body. Without the fasteners to hold the mesh in place, the mesh may come loose. These events may lead to additional complications, and possibly additional surgery.

Numerous attempts have been made to provide hernia meshing systems and methods of implanting a mesh panel around the hernia. Even though these innovations may be suitable for the specific purposes to which they address, however, they would not be as suitable for the purposes of the present invention.

For example, U.S. Pat. Nos. 6,171,318 and 6,290,708 to Kugel et al. disclose a hernia patch having two layers of inert synthetic mesh material joined together by a seam to form a pouch between the layers. The pouch houses a stiffening layer to provide stiffness to the patch. Further, an access slit in one of the layers allows insertion of a surgeon's finger or instrument into the pouch.

U.S. Pat. No. 6,425,900 to Knodel et al. teaches a method for use of the surgical fastening instrument and surgical fastener in combination with a prosthetic for the repair of an inguinal hernia.

U.S. Pat. No. 8,216,272 to Shipp describes a delivery device for delivering at least one surgical anchor and fastener into a patient's tissue. The device comprises a housing, a delivery tube and a reciprocating absorbable mesh anchor. Further it teaches a method of forming an absorbable mesh fixation anchor that exhibits a known absorption time and that exhibits the mechanical properties adequate for the desired fixation strength and the required implant forces.

U.S. Pat. Application No. 20160074034 to Shipp discloses a fastener applier apparatus and method of forming and deploying absorbable fasteners for hernia mesh fixation. The absorbable fastener functions to securely fasten tough, non-macro-porous, and relative inelastic mesh to soft tissue. The fastener is formed from co-polymers of lactide and glycolide.

U.S. Pat. Nos. 8,343,176, 8,852,215 and 9,486,218 to Crisuolo et al. disclose absorbable surgical tacks and insertion instruments for inserting one or more hernia tacks through mesh and into tissue during a hernia repair.

U.S. Pat. No. 8,500,759 to Koyfman et al. describes a surgical device for repairing a hernia, the device has self-anchoring means that securely attaches to the peritoneum or pre-peritoneal layers, while protecting abdominal organs.

U.S. Pat. Nos. 8,500,762 and 9,642,689 to Sholev et al. teach a hernia repair kit having an inflatable balloon type mesh deployment device and a fixating component comprising a coil that is spontaneously reconfigurable from a retracted position to an un-retracted position.

U.S. Pat. Application No. 20020103494 to Pacey describes a cannula delivery system for hernia patch comprising a metal reinforced plastic fabric patch that is introduced into the hernial defect by use of a cannula to expand and deploy the patch, wherein the patch is capable of stabilizing the peritoneum by use of a radiating skeleton with polydirectional hooks.

U.S. Pat. Application No. 20110106113 to Tavakkolizadeh et al. teaches a surgical fastener and associated deployment system to fixate a surgical mesh material to the abdominal wall for the purpose of hernia repair. The fastener includes an anchor head comprising a bi-pyramid framework. The anchor head may be provided in an elongate, undeployed configuration, and then expanded during deployment into planar configuration.

It is apparent now that numerous innovations that are adapted to a hernia meshing system and method have been developed in the prior art that are adequate for various purposes. Furthermore, even though these innovations may be suitable for the specific purposes to which they address, accordingly, they would not be suitable for the purposes of the present invention as heretofore described. Thus a ventral hernia meshing system used to fixate a surgical mesh panel to an abdominal wall for the purpose of hernia repair and prevention of hernia recurrence at the peripheral region of the mesh panel is needed.

SUMMARY OF THE INVENTION

The present invention relates to a ventral hernia meshing system used to fixate a surgical mesh panel to an abdominal wall for the purpose of hernia repair and prevention of hernia recurrence at the peripheral region of the mesh panel; whereby the mesh panel comprises a hydrophilic face and a meshed face; whereby a plurality of hollow anchors such as spikes or pins or hooks are disposed along the peripheral region of the mesh panel in a spaced apart relationship, exposing the meshed face to a herniated area; whereby a blunt quill or needle, or the surgeons hand, presses the hollow anchors into the fascia around the hernia, and then removed after pressing the hollow pin into the fascia, such that there is no sharp needle or suture used; whereby tissue grows into the cavity of the hollow anchors to provide a sutureless anchor and further enable a larger mesh panel.

According to an aspect of the present invention, a tissue aperture sutureless repair meshing system particularly a ventral hernia meshing system for implanting within a patient, the system comprising a mesh panel defined by a hydrophilic face and an opposite meshed face, wherein both the faces are joined around a peripheral region, further the hydrophilic face engages the tissue of a tissue aperture affected area; a plurality of hollow anchors defined by a distal end, a proximal end, and a continuous cavity running between the distal end and the proximal end, wherein, the proximal end of the hollow anchors are disposed along the peripheral region of the mesh panel in a spaced apart relationship; and a blunt pressing means for pressing the distal end of the hollow anchors into a fascia around the tissue aperture affected area, the blunt pressing means being removed after pressing the distal end of the hollow anchors into the fascia, whereby tissue grows in the cavity of the hollow anchors to provide a sutureless anchor in fixing the mesh panel around the tissue aperture affected area.

In view of the foregoing, it is therefore an objective of the present invention is to repair a hernia without use of a suture.

Another objective is to fixate a surgical mesh panel to an abdominal wall for the purpose of hernia repair and prevention of hernia recurrence at the peripheral region of the mesh panel.

Another objective is to firmly anchor the peripheral region of the mesh panel to the herniated area.

Another objective is to use a blunt needle to press the hollow anchors into the tissue around the hernia.

Yet another objective is to provide an inexpensive to manufacture sutureless ventral hernia meshing system.

Other objectives and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1A:
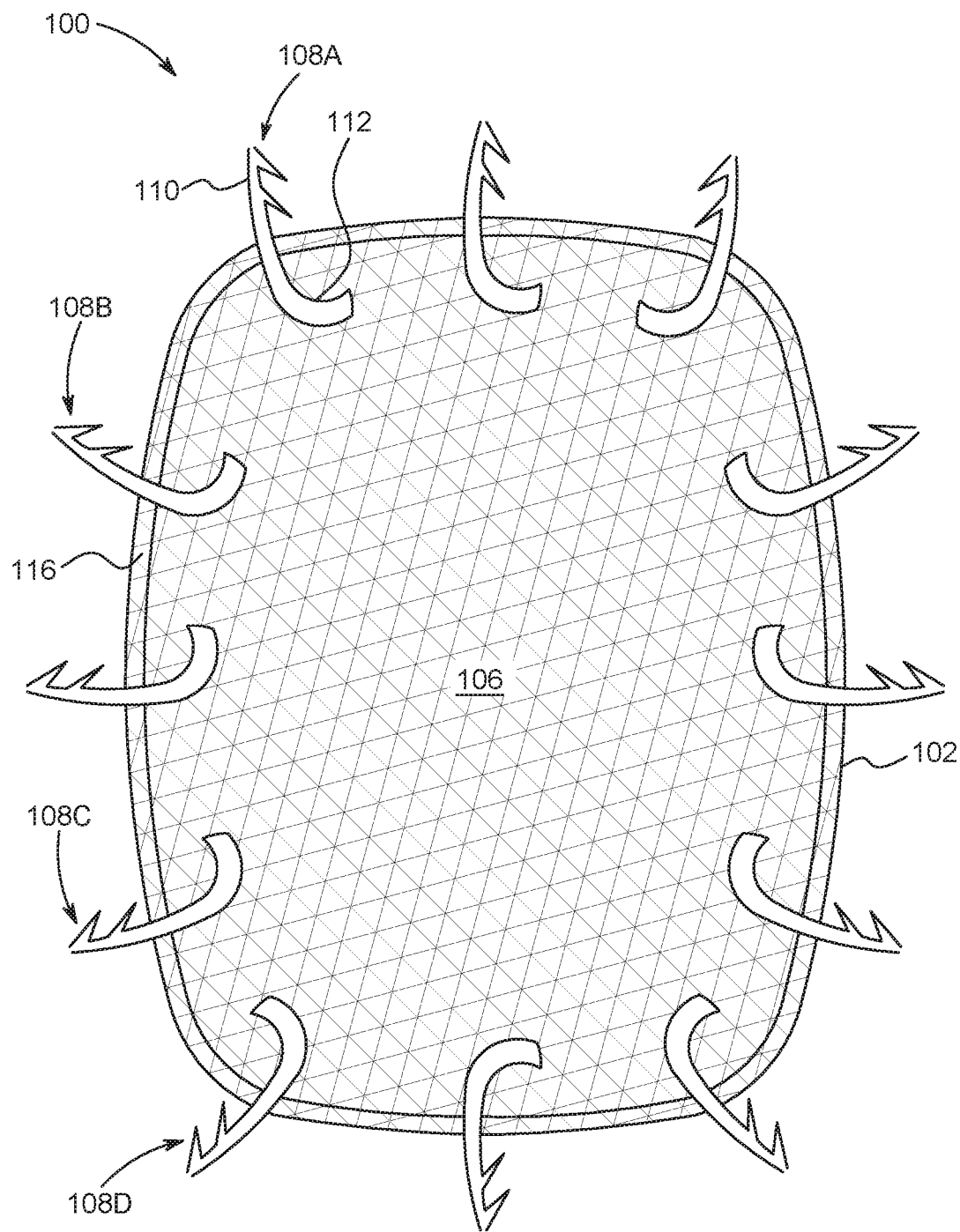
FIG. 1A illustrates a top perspective view of a sutureless ventral hernia meshing system having an exemplary mesh panel attached with hollow anchors, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A sutureless ventral hernia meshing system 100 and a method 200 of fixation is referenced in FIGS. 1A-6. The sutureless ventral hernia meshing system 100, hereafter "system 100", is efficacious for fixating a surgical mesh panel 102 to an abdominal wall or fascia (not shown) for the purpose of hernia repair and prevention of hernia recurrence at the peripheral region 116 of the mesh panel 102.

In some embodiments, the mesh panel 102 may include a hydrophilic face 104, a meshed face 106, and a peripheral region 116 that creates a boundary around the herniated area. A plurality of hollow anchors such as spikes or pins or hooks 108A-D are disposed along the peripheral region 116 of the mesh panel 102 in a spaced apart relationship. In one embodiment, twelve spikes or pins or hooks 108A-D are used, however more or less number of spikes or pins or hooks 108A-D or the like may be used without departing from the scope and spirit of the present invention. The anchors 108A-D extend from the meshed face 106 side of the mesh panel 102, and may form a curved configuration of enhanced anchoring capacity.

A blunt pressing means 118 such as a quill or a needle, or a surgeon's hand, may be used to press the hollow anchors 108A-D into the fascia around the hernia. The blunt quill or needle 118 is removed after pressing the hollow pin into the fascia. In this manner, no sharp needle or suture is used. As a consequence of the hollow anchors 108A-D, tissue grows into the cavity 114 of the hollow anchors 108A-D to provide a sutureless anchor, and thereby fixate the mesh panel 102 around the herniated area. Another advantage provided by the system 100 is that a larger dimensioned mesh panel 102 can be used because the peripheral region 116 firmly anchors into the fascia tissue around the herniated area.

According to an aspect of the present invention, a tissue aperture sutureless repair meshing system 100 for implanting a mesh panel within a patient, the system 100 comprising a mesh panel 102 defined by a hydrophilic face 104, an opposite meshed face 106 and a peripheral region 116, further the hydrophilic face 104 engages the tissue of a tissue aperture affected area; a plurality of hollow anchors 108A-D defined by a distal end 110, a proximal end 112, and a continuous cavity 114 running between the distal end 110 and the proximal end 112, wherein, the proximal end 112 of the hollow anchors 108A-D are disposed along the peripheral region 116 of the mesh panel 102 in a spaced apart relationship; and a blunt pressing means 118 for pressing the distal end 110 of the hollow anchors 108A-D into a fascia around the tissue aperture affected area, the blunt pressing means 118 being removed after pressing the distal end 110 of the hollow anchors 108A-D into the fascia, whereby tissue grows in the cavity 114 of the hollow anchors 108A-D to provide a sutureless anchor in fixing the mesh panel 102 around the tissue aperture affected area.

In another aspect, the system 100 negates the need for a suture.

In another aspect, the plurality of hollow anchors 108A-D is selected from the group consisting of spikes or pins or hooks.

In another aspect, the system 100 comprises twelve hollow anchors 108A-D.

In another aspect, the cross section of the hollow anchor 108A-D is circular.

In another aspect, the hollow anchors 108A-D are defined by a cylindrical volume and smooth sidewall surfaces to from the cavity 114.

In another aspect, the blunt pressing means 118 is selected from the group consisting of a blunt quill or a blunt needle or a surgeon's hand.

In another aspect, the mesh panel 102 is a medically sterile, thin, flexible material.

In another aspect, the distal end 110 of the hollow anchors 108A-D is tapered.

In another aspect, the distal end 110 of the hollow spikes or pins or hooks 108A-D anchor into the fascia.

In another aspect, the hydrophilic face 104 of the mesh 102 and cavity 114 of the hollow anchors 108A-D of the system allows tissue to grow over of the hydrophilic face 104 of the mesh 102 and easily expand into the cavity 114 of the hollow anchors 108A-D, thereby allowing to use mesh panel size of 12 square centimeter or larger.

According to another aspect, the system is more particularly useful for sutureless implantation of the mesh panel 102 to repair a hernia. Thus according to an exemplary embodiment, a sutureless ventral hernia meshing system 100, the system 100 comprising, a medically sterile and flexible mesh panel 102 defined by a hydrophilic face 104, an opposite meshed face 106 and a peripheral region 116, further the hydrophilic face 104 engages the tissue of a herniated area; a plurality of hollow spikes 108A-D defined by a distal end 110, a proximal end 112, and a continuous tapered cavity 114 running between the distal end 110 and the proximal end 112, wherein, the proximal end 112 of the hollow spikes 108A-D are disposed along the peripheral region 116 of the mesh panel 102 in a spaced apart relationship; and a blunt pressing means such as a surgeon's hand 118 for pressing the distal end 110 of the hollow spikes 108A-D into a fascia around the herniated area, wherein, the surgeon removes his hand or the blunt pressing means after pressing the distal end 110 of the hollow spikes 108A-D into the fascia, whereby tissue grows over of the hydrophilic face 104 of the mesh 102 and easily expand into the cavity 114 of the hollow spikes 108A-D to provide a sutureless anchor in fixing the mesh panel 102 around the herniated area, thereby allowing to use mesh panel size of 12 square centimeter or larger.

One objective of the present invention is to repair a hernia without use of a suture.

Another objective is to fixate a surgical mesh panel 102 to an abdominal wall for the purpose of any tissue aperture repair, such as hernia repair and prevention of hernia recurrence at the peripheral region 116 of the mesh panel 102.

Another objective is to firmly anchor the peripheral region 116 of the mesh panel 102 to the herniated area.

Another objective is to use a blunt needle 118 to press the hollow spikes or pins or hooks 108A-D into the tissue around the hernia.

Yet another objective is to provide an inexpensive to manufacture sutureless ventral hernia meshing system 100.

According to an embodiment of the present invention as referenced in FIG. 1A, a sutureless ventral hernia meshing system 100 comprises a mesh panel 102 defined by a hydrophilic face 104 (shown in FIGS. 1A and 2A), a meshed face 106 and a peripheral region 116 that creates a boundary around the herniated area. In one embodiment, the mesh panel 102 is a thin, flexible material. The mesh panel 102 may also be medically sterile. The hydrophilic face 104 of the mesh panel 102 engages the tissue of the herniated area. The meshed face 106 faces outwardly and supports the hollow anchors 108A-D such as spikes, pins, hooks and the like along the peripheral region 116 of the mesh panel 102.

Figure 2A:
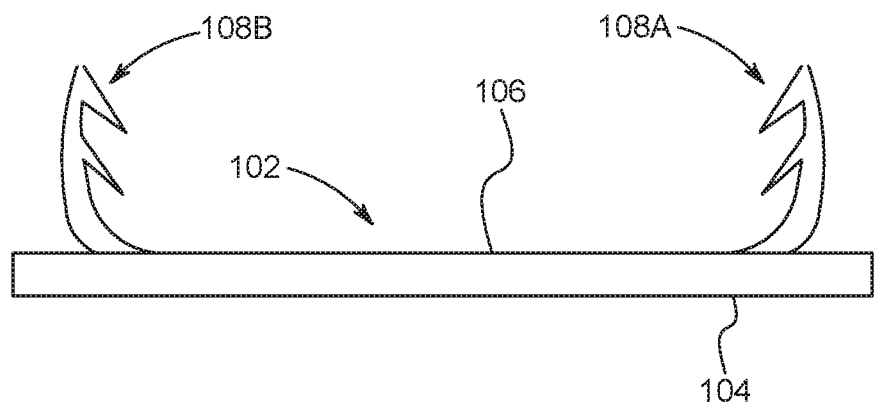
FIG. 2A, illustrates a side view of the exemplary sutureless ventral hernia meshing system as shown in FIG. 1A, in accordance with an embodiment of the present invention.

Turning now to FIG. 2A, which is a side view of the exemplary sutureless ventral hernia meshing system 100 as shown in FIG. 1A, the hollow anchors 108A-D are defined by a distal end 110, a proximal end 112, and a cavity 114. The hollow anchors 108A-D are disposed along the peripheral region 116 of the mesh panel 102 in a spaced apart relationship. The hollow spikes or pins or hooks 108A-D extend from the meshed face 106 side of the mesh panel 102. The hollow anchors 108A-D may have a tapered distal end 110 that is configured to facilitate penetration into the fascia tissue. The cross section of the hollow anchors 108A-D may be circular.

Figure 1B:
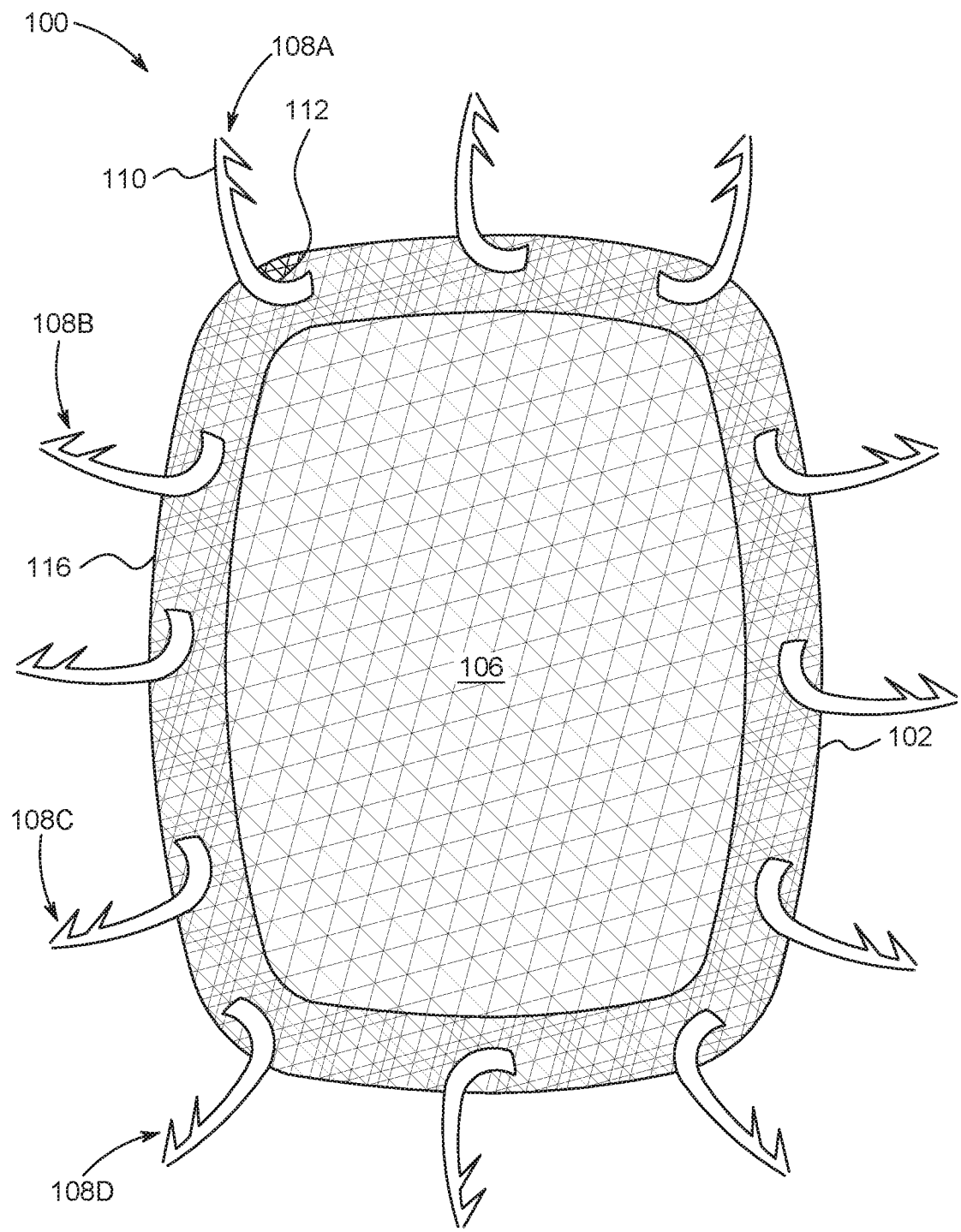
FIG. 1B illustrates a top perspective view of a sutureless ventral hernia meshing system having an exemplary mesh panel forming a shallow pouch configuration attached with hollow anchors, in accordance with an embodiment of the present invention.

According to another exemplary embodiment of the present invention as referenced in FIG. 1B, a sutureless ventral hernia meshing system 100 comprises a mesh panel 102 defined by a hydrophilic face 104 (shown in FIGS. 1A and 2A), a meshed face 106 and a peripheral region 116 that is configured to form a shallow pouch of the mesh panel 102 so as to creates a boundary around the herniated area, thereby allowing sufficient space for a surgeon's hand to press the hollow anchors 108A-D into the fascia around the hernia. The hydrophilic face 104 of the mesh panel 102 engages the tissue of the herniated area. The meshed face 106 faces outwardly and supports the hollow anchors 108A-D such as spikes, pins, hooks and the like along the peripheral region 116 of the mesh panel 102.

Figure 2B:
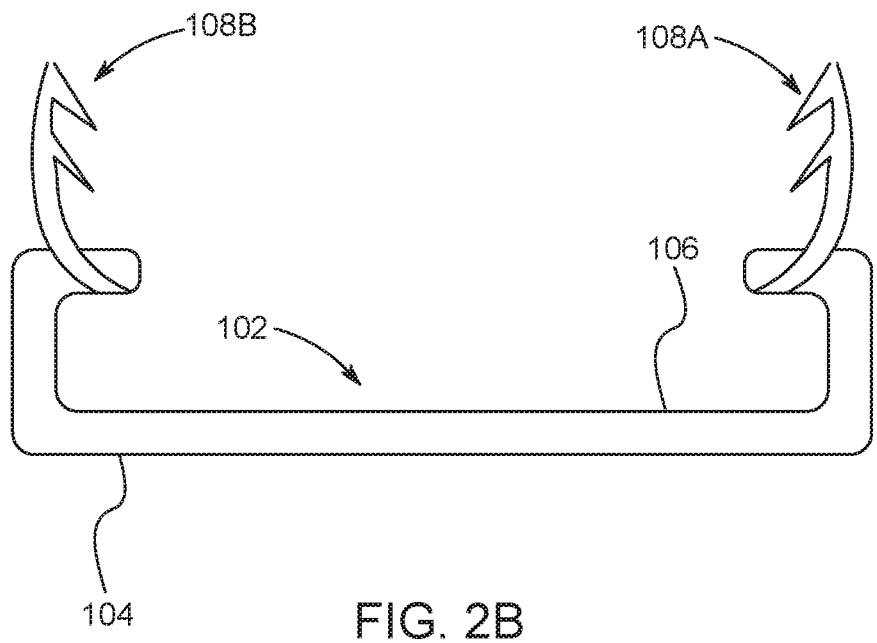
FIG. 2B, illustrates a side view of the exemplary sutureless ventral hernia meshing system as shown in FIG. 1B, in accordance with an embodiment of the present invention.

Turning now to FIG. 2B, which is a side view of the exemplary sutureless ventral hernia meshing system 100 as shown in FIG. 1B, the hollow anchors 108A-D are defined by a distal end 110, a proximal end 112, and a cavity 114. The hollow anchors 108A-D are disposed along the peripheral region 116 of the mesh panel 102 in a spaced apart relationship. The hollow spikes or pins or hooks 108A-D are disposed along the peripheral region 116 of the mesh panel 102. The hollow anchors 108A-D may have a tapered distal end 110 that is configured to facilitate penetration into the fascia tissue.

Figure 3A:
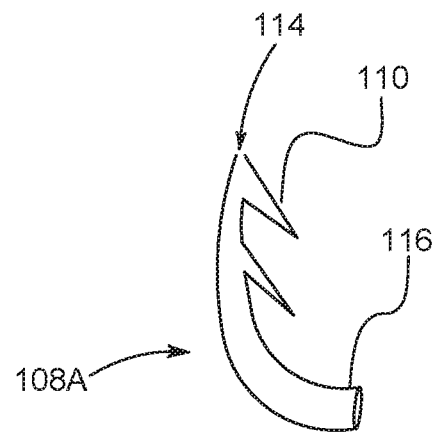
FIG. 3A illustrates a close up front view of an exemplary hollow anchor, in accordance with an embodiment of the present invention.
Figure 3B:
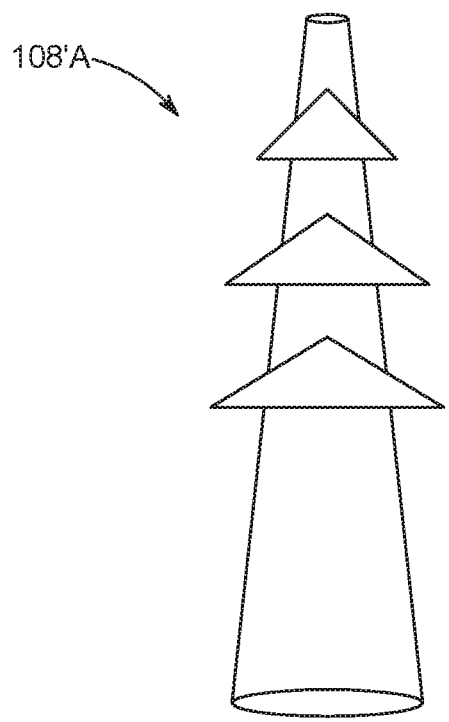
FIG. 3B illustrates a close up front view of another exemplary hollow anchor, in accordance with an embodiment of the present invention.

As shown in FIG. 3A, the hollow anchors 108A-D such as hollow spikes or pins or hooks may have a straight or curved configuration. Though other shapes of the hollow anchors 108A-D, which are conducive to anchoring into the fascia tissue may be used, including a rectangular shape, a pyramidal shape, and a block shape. In an exemplary embodiment a pyramidal shaped hollow anchor 108'A is illustrated in FIG. 3B. The hollow anchors 108A-D are defined by a cylindrical volume and smooth sidewall surfaces that from a cavity 114. The cavity 114 may have a circular cross section, and is configured to enable tissue to grow inside the hollow anchors 108A-D. This anchoring capacity allows the tissue at the perimeter of the mesh panel 102 to anchor firmly. These dimensions and textures of the sidewalls and cavity 114 allow tissue to easily expand into the volume of the cavity during growth.

Figure 4:
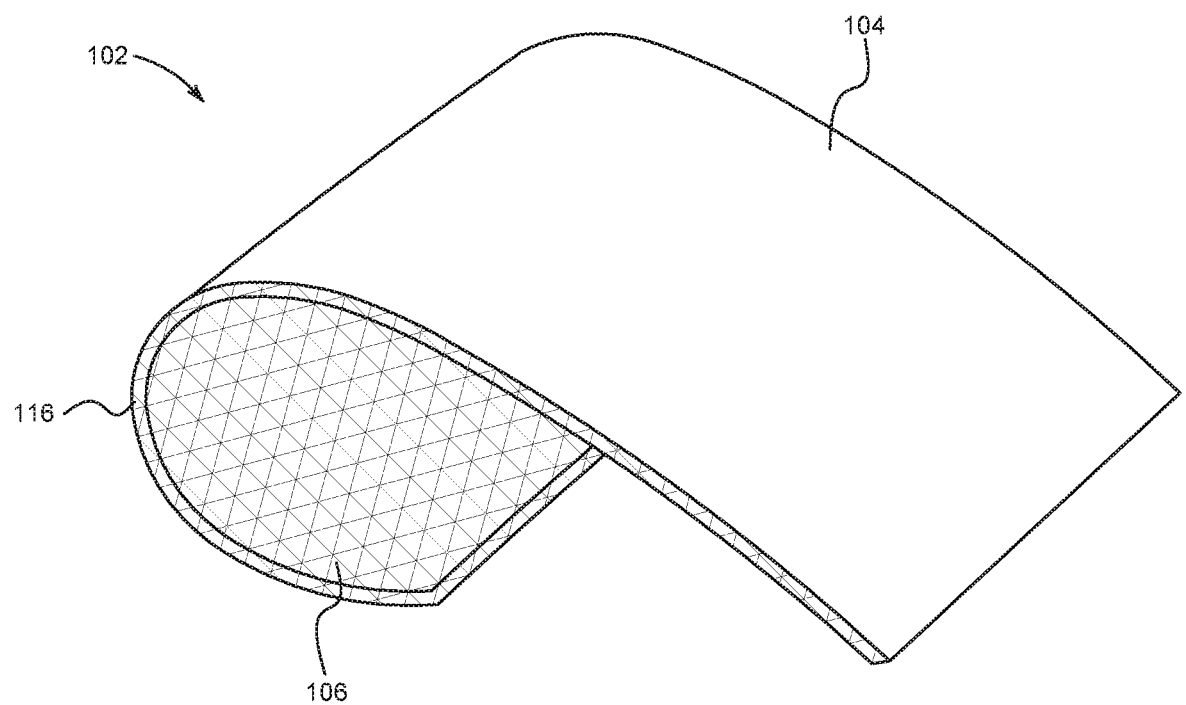
FIG. 4 illustrates a perspective view of an exemplary mesh panel showing both meshed face and hydrophilic face of the mesh panel, in accordance with an embodiment of the present invention.

FIG. 4 illustrates a perspective view of an exemplary mesh panel 102 showing both meshed face 106 and hydrophilic face 104 of the mesh panel 102, in accordance with an embodiment of the present invention.

Figure 5:
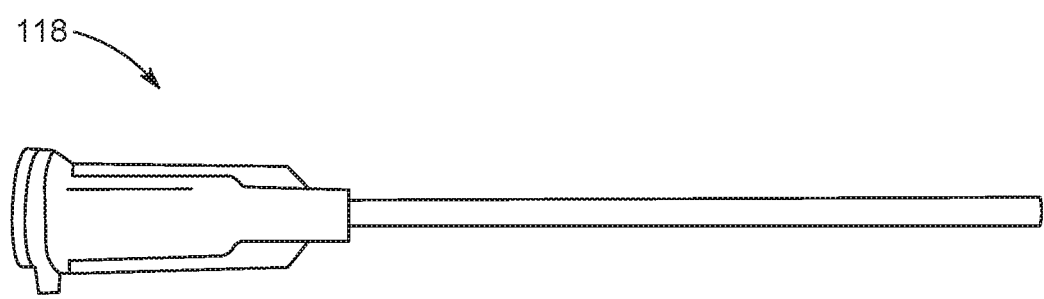
FIG. 5 illustrates a side view of an exemplary blunt needle or quill, in accordance with an embodiment of the present invention.

As FIG. 5 illustrates, a blunt quill or needle 118 may be used for pressing the hollow anchors such as spikes or pins or hooks 108A-D into a fascia around the hernia area. In other embodiments, a surgeon's hand may be used to press the hollow anchors 108A-D into a fascia around the hernia area. The blunt quill or needle 118 is removed after pressing the hollow anchors 108A-D into the fascia. In this manner, the hollow anchors 108A-D are implanted in the abdominal wall/fascia of the patient, so that tissue grows in the cavity 114 of the hollow anchors 108A-D, creating a firm anchor of the mesh panel 102 to the herniated area. Thus, sutureless repair meshing system 100 of the present invention for implanting a mesh panel 102 into the boundary 116 around the hernia region, thereby preventing recurrence of the hernia at the periphery of the mesh 102.

According to another embodiment of the present invention, the hollow spikes or the like allow to position the mesh panel 102 at its periphery and thus allows much larger meshes to be used, so that there will be no overlap of the fascia. In an exemplary embodiment the system 100 of the present invention facilitates the hydrophilic face 104 of the mesh 102 and cavity 114 of the hollow anchors 108A-D allows tissue to grow over of the hydrophilic face 104 of the mesh 102 and easily expand into the cavity 114 of the hollow anchors 108A-D, thereby allowing to use mesh panel size of 12 square centimeter or larger.

According to another embodiment of the present invention, the sutureless repair meshing system 100 comprises at least a mesh 102 and a plurality of spikes 108A-D as a kit to be used for at least hernia repair works or other related tissue aperture repair works. Further the system 100 of the present invention allows easier, quicker and correct implantation of the mesh panel 102 at the herniated area so as to provide a permanent solution and a wider coverage of the herniated area.

Figure 6:
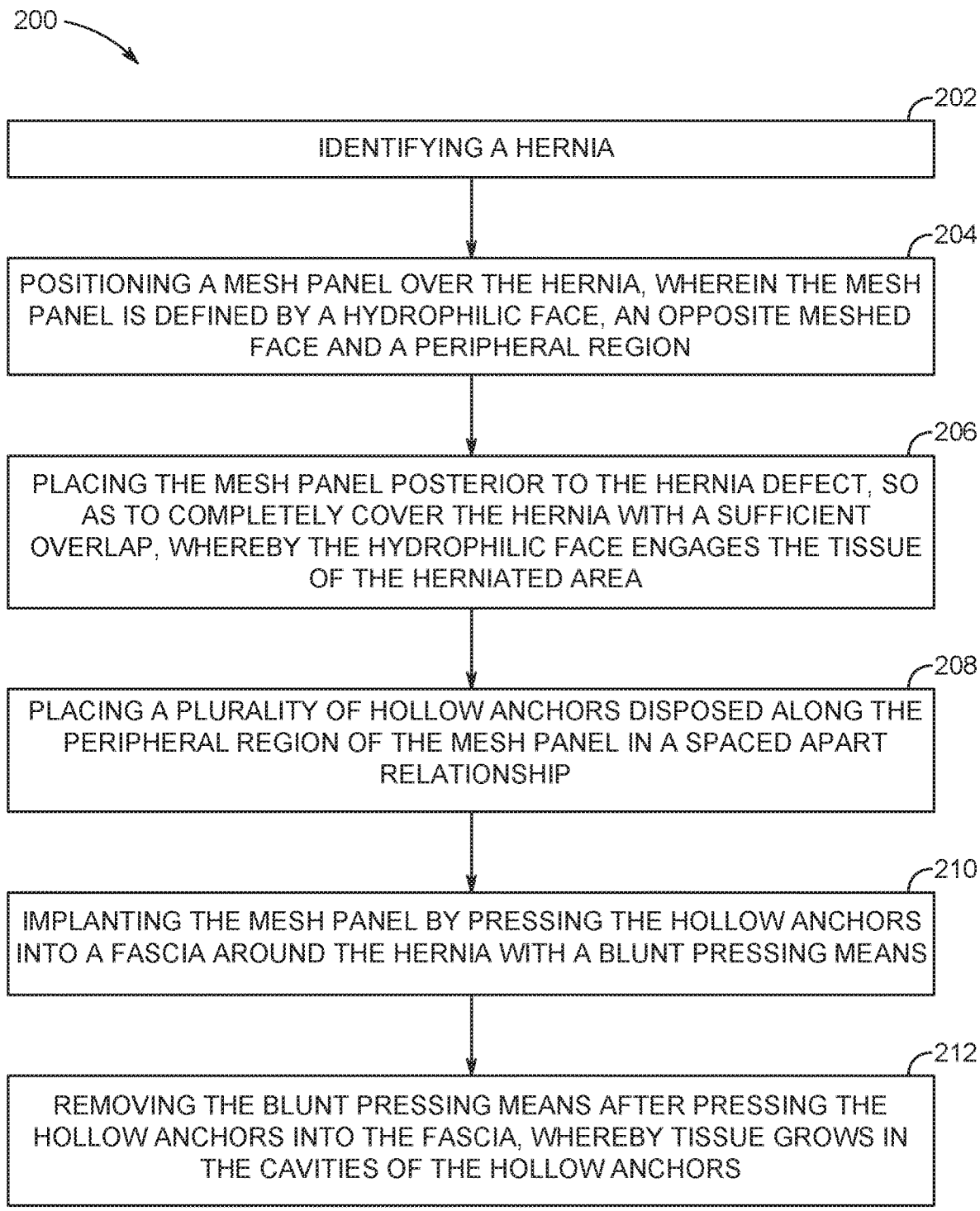
FIG. 6 illustrates a flowchart of an exemplary method for fixating a sutureless ventral hernia meshing system to a herniated area, in accordance with an embodiment of the present invention.

According to another aspect of the present invention as shown in FIG. 6 that illustrates a flowchart of an exemplary method 200 for fixating a sutureless ventral hernia meshing system to a herniated area. The method 200 may include an initial Step 202 of identifying a hernia. The method 200 may further comprise a Step 204 of positioning a mesh panel over the hernia, wherein the mesh panel is defined by a hydrophilic face, an opposite meshed face and a peripheral region, whereby the plurality of hollow anchors defined by a distal end, a proximal end, and a cavity extending between the distal end and the proximal end. A Step 206 includes placing the mesh panel posterior to the hernia defect, so as to completely cover the hernia with a sufficient overlap, whereby the hydrophilic face engages the tissue of a herniated area. Step 208 comprises placing a plurality of hollow anchors disposed along the peripheral region of the mesh panel in a spaced apart relationship. A Step 210 comprises implanting the mesh panel by pressing the distal end of the hollow anchors into a fascia around the hernia with a blunt pressing means such as a blunt quill or a blunt needle or a surgeon's hand. A Step 212 includes removing the blunt pressing means after pressing the distal end of the hollow anchors into the fascia, whereby tissue grows in the cavity of the hollow anchors to provide a sutureless anchor in fixating the mesh panel around the herniated area.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A tissue aperture sutureless repair meshing system for implanting a mesh panel within a patient, the system comprising:
   a mesh panel defined by a hydrophilic face, an opposite meshed face and a peripheral region, further the hydrophilic face is configured to engage the tissue of a tissue aperture affected area;
   a plurality of hollow anchors defined by a distal end, a proximal end, and a continuous tapered cavity running between the distal end and the proximal end, wherein the proximal end of the hollow anchors are disposed along the peripheral region of the mesh panel in a spaced apart relationship, wherein the hollow anchors extend from the meshed face of the mesh panel, and form a curved configuration of enhanced anchoring capacity; and
   a blunt pressing means for pressing the distal end of the hollow anchors into a fascia around the tissue aperture affected area, the blunt pressing means being removed after pressing the distal end of the hollow anchors into the fascia,
   whereby tissue is configured to grow in the cavity of the hollow anchors to provide a sutureless anchor in fixing the mesh panel around the tissue aperture affected area.

2. The system of claim 1, wherein the plurality of hollow anchors are selected from the group consisting of spikes or pins or hooks.

3. The system of claim 1, wherein the system comprises twelve anchors.

4. The system of claim 1, wherein the blunt pressing means is selected from the group consisting of a blunt quill or a blunt needle.

5. The system of claim 1, wherein the mesh panel is made of a medically sterile and flexible material.

6. The system of claim 1, wherein the distal end of each of the hollow anchors is tapered.

7. The system of claim 1, wherein the cross section of the hollow anchor is circular.

8. The system of claim 1, wherein the hollow anchors are defined by a cylindrical volume and smooth sidewall surfaces of the cavity.

9. The system of claim 1, wherein the hydrophilic face of the mesh panel and cavity of the hollow anchors of the system allows tissue to grow over the hydrophilic face of the mesh and expand into the cavity of the hollow anchors, whereby the hollow anchors allow the use of a mesh panel size of 12 square centimeter or larger.

10. A sutureless ventral hernia meshing system, the system comprising:
    a medically sterile and flexible mesh panel defined by a hydrophilic face, an opposite meshed face and a peripheral region, further the hydrophilic face is configured to engage the tissue of a herniated area;
    a plurality of hollow spikes defined by a distal end, a proximal end, and a continuous tapered cavity running between the distal end and the proximal end, wherein, the proximal end of the hollow spikes are disposed along the peripheral region of the mesh panel in a spaced apart relationship; and
    a blunt pressing means for pressing the distal end of the hollow spikes into a fascia around the herniated area, wherein, the blunt pressing means is removed after the distal end of the hollow spikes are pressed into the fascia,
    whereby tissue is configured to grow over of the hydrophilic face of the mesh and expand into the cavity of the hollow spikes to provide a sutureless anchor in fixing the mesh panel around the herniated area, whereby the sutureless anchor allows the use of a mesh panel size of 12 square centimeter or larger.

11. The system of claim 10, wherein the system comprises at least twelve anchors.

12. The method of claim 10, wherein the hollow spikes are defined by a cylindrical volume having a circular cross section and smooth sidewall surfaces of the cavity, further the spikes have a tapered configuration from the proximal end to the distal end.

13. The system of claim 10, wherein the peripheral region of the mesh panel is symmetrically folded inward to form a shallow pouch of the mesh panel so as to create a boundary around the herniated area while allowing sufficient space for a surgeon's hand to press the hollow anchors into the fascia around the hernia.

14. A method for fixating a sutureless ventral hernia meshing system to a herniated area, the method comprising:
    identifying a hernia;
    positioning a mesh panel over the hernia, wherein the mesh panel is defined by a hydrophilic face, an opposite meshed face, a plurality of hollow anchors, and a peripheral region, whereby the plurality of hollow anchors are defined by a distal end, a proximal end, and a cavity extending between the distal end and the proximal end;
    placing the mesh panel posterior to the hernia defect, so as to completely cover the hernia with a sufficient overlap, whereby the hydrophilic face engages the tissue of the herniated area;
    placing the plurality of hollow anchors disposed along the peripheral region of the mesh panel in a spaced apart relationship;
    implanting the mesh panel by pressing the distal end of the hollow anchors into a fascia around the hernia with a blunt pressing means; and
    removing the blunt pressing means after pressing the distal end of the hollow anchors into the fascia, whereby tissue grows in the cavity of the hollow anchors to provide a sutureless anchor in fixating the mesh panel around the herniated area.

15. The method of claim 14, wherein the plurality of hollow anchors are selected from the group consisting of spikes or pins or hooks.

16. The method of claim 14, wherein at least twelve anchors are used to hold the mesh panel to the fascia around the hernia.

17. The method of claim 14, wherein the blunt pressing means is selected from the group consisting of blunt quill or a blunt needle or a surgeon's hand.

18. The method of claim 14, wherein the mesh panel is made of a medically sterile and flexible material.

19. The method of claim 14, wherein the hollow anchors having a tapered configuration from the proximal end to the distal end.

20. The method of claim 14, wherein the hydrophilic face of the mesh and cavity of the hollow anchors of the system allows tissue to grow over of the hydrophilic face of the mesh and expand into the volume of the cavity of the hollow anchors, whereby the hollow anchors allow the use of a mesh panel size of 12 square centimeter or larger.

* * * * *